(12) United States Patent
Mougin

(10) Patent No.: US 6,805,872 B2
(45) Date of Patent: Oct. 19, 2004

(54) USE IN COSMETICS OF BLOCK ETHYLENE COPOLYMERS WITH ELASTIC CHARACTER AND COMPOSITIONS CONTAINING SAME

(75) Inventor: Nathalie Mougin, Paris (FR)

(73) Assignee: L'Oreal, Paris (FR)

( * ) Notice: Subject to any disclaimer, the term of this patent is extended or adjusted under 35 U.S.C. 154(b) by 63 days.

(21) Appl. No.: 10/031,233

(22) PCT Filed: May 18, 2001

(86) PCT No.: PCT/FR01/01525

§ 371 (c)(1),
(2), (4) Date: Jan. 17, 2002

(87) PCT Pub. No.: WO01/89470

PCT Pub. Date: Nov. 29, 2001

(65) Prior Publication Data

US 2002/0115780 A1 Aug. 22, 2002

(30) Foreign Application Priority Data

May 23, 2000 (FR) .............................. 00 06534

(51) Int. Cl.⁷ ............................. A61K 6/00; A61K 7/00; A61K 31/74; A61K 7/06; A61K 7/11
(52) U.S. Cl. ................... 424/401; 424/70.1; 424/70.11; 424/70.16; 424/78.02; 424/78.03; 424/78.18
(58) Field of Search ................ 424/401, 70.1, 424/70.11, 70.16, 78.02, 78.03, 78.18

(56) References Cited

U.S. PATENT DOCUMENTS 4,726,942 A * 2/1988 Lang et al. .................... 424/47
5,264,527 A * 11/1993 Varshney et al. ........... 525/299
5,711,940 A 1/1998 Kuentz et al.

FOREIGN PATENT DOCUMENTS

| FR | 2 743 640 A | 10/1997 |
|---|---|---|
| WO | 00 40628 A | 7/2000 |
| WO | 00 71591 A | 11/2000 |

* cited by examiner

*Primary Examiner*—Sreeni Padmanabhan
*Assistant Examiner*—Lauren Q Wells
(74) *Attorney, Agent, or Firm*—Nixon & Vanderhye P.C.

(57) ABSTRACT

The invention relates to the cosmetic use of block ethylenic copolymers of elastic nature comprising at least one rigid block having a glass transition temperature ($T_g$) of greater than or equal to 20° C. and at least one flexible block having a glass transition temperature ($T_g$) which is less than 20° C., said compolymers making it possible to obtain a film having an instantaneous recovery of between 5% and 100%. The invention also relates to cosmetic compositions containing these block ethylenic polymers of elastic nature.

51 Claims, No Drawings

USE IN COSMETICS OF BLOCK ETHYLENE COPOLYMERS WITH ELASTIC CHARACTER AND COMPOSITIONS CONTAINING SAME

This application is the US national phase of international application PCT/FR01/01525 filed 18 May 2001, which designated the US.

The present invention relates to the cosmetic use of block ethylenic copolymers of elastic nature and also to cosmetic compositions containing such copolymers.

Certain block copolymers are known as being thermoplastic elastomers, that is to say polymers combining the elasticity of a vulcanized rubber with hot plasticity or hot meltability (Thermoplastic Elastomers: Comprehensive Review, Legge N. R., Holden G., published by Hense Munich, 1987).

The elastic properties of this type of polymer derive from the combination of at least one "flexible" block providing the elastic properties, and of at least one "rigid" block providing, by self-association, the reversible physical crosslinking of the macromolecular chains.

Patent application WO 98/38981 discloses hydrocarbon-based solvent gels containing thermoplastic elastomers and especially styrene/butadiene/styrene, styrene/isoprene/styrene and styrene/ethylene/butylene/styrene block copolymers sold by Shell Chemical Company under the name Kraton®. In these hydrocarbon-based media, the copolymers act as thickener and gelling agent, which does not allow them to be formulated in high contents.

These polymers also have the drawback of being insoluble in most of the solvents used cosmetically, such as alcohols, ethers, esters and/or water. Moreover, the synthesis of these block copolymers is carried out by anionic polymerization, which is a method that is difficult to implement.

New free-radical polymerization techniques have recently been developed, such as controlled polymerization ("New Method of Polymer Synthesis", Blackie Academic & Professional, London, 1995, volume 2, page 1, or Trends Polym. Sci. 4, page 183 (1996) by C. J. Hawker), and especially atom-transfer free-radical polymerization (JACS, 117, page 5614 (1995), by Matyjasezwski et al.). These techniques now make it possible to perform the free-radical synthesis of a very wide variety of block copolymers "to order" under operating conditions that are more readily industrializable than was the case for anionic or cationic polymerization, and thus allow an adjustment of the physicochemical properties of the polymers according to the intended use.

By incorporating these novel block copolymers into cosmetic compositions, the Applicant has discovered that certain block ethylenic copolymers of elastic nature described in greater detail hereinbelow have very advantageous cosmetic properties. In general, they produce non-stick systems. When used in hair lacquers, they improve both the styling power and the suppleness of the hair lacquers. They increase the impact strength of nail varnishes and improve the staying power of a wide variety of make-up compositions if without causing the user any discomfort.

One subject of the invention is, consequently, the cosmetic use of block ethylenic copolymers of elastic nature, comprising
 (a) at least one rigid block having a glass transition temperature ($T_g$) of greater than or equal to 20° C., consisting of units derived from one or more ethylenic monomers, and
 (b) at least one flexible block having a glass transition temperature ($T_g$) of less than 20° C., consisting of units derived from one or more ethylenic monomers,
said copolymers allowing the production of a film having an instantaneous recovery of between 5% and 100% with the exclusion of block copolymers having flexible blocks consisting exclusively of ethylene, propylene, butylene, butadiene and/or isoprene units.

The subject of the invention is also cosmetic compositions comprising these block ethylenic copolymers of elastic nature.

Another subject of the invention is the use of the block ethylenic copolymers of elastic nature comprising at least one rigid block and having a glass transition temperature ($T_g$) of greater than or equal to 20° C. and at least one flexible block having a glass transition temperature ($T_g$) of less than 20° C., to improve the suppleness and the styling power of a hair lacquer, to increase the impact strength of a nail varnish or to improve the staying power of a make-up composition.

Other subjects will become apparent on reading the description and the examples which follow.

The expression "units derived from a monomer" as used in the present invention denotes the constituent units of the polymer obtained by polymerization of said monomer.

The block ethylenic copolymers used cosmetically in accordance with the invention are copolymers comprising at least two blocks of monomers that differ as regards their glass transition temperature, one having a glass transition temperature which is greater than or equal to room temperature (20° C.), and the other having a glass transition temperature which is less than room temperature. The first type of block is generally termed "rigid" since, at room temperature, this part of the polymer is in the glassy state, whereas the second type of block, which is in the plastic state at room temperature, is referred to as being "flexible".

As mentioned above, these block ethylenic copolymers of elastic nature are preferably obtained by controlled free-radical polymerization described, inter alia, in "New Method of Polymer Synthesis", Blackie Academic & Professional, London 1995, volume 2, page 1, or in Trends Polym. Sci. 4, page 183 (1996) by C. J. Hawker.

Controlled free-radical polymerization makes it possible to reduce the deactivation reactions of the growing free-radical species, in particular the termination step, these being reactions which, in standard free-radical polymerization, interrupt the growth of the polymer chain in an irreversible and uncontrolled manner.

In order to reduce the probability of the termination reactions, it has been proposed to transiently and reversibly block the growing free-radical species by forming "dormant" active species in the form of a bond with a low dissociation energy.

Thus, the polymerization may be performed according to the atom-transfer technique or by reaction with a nitroxide, or alternatively according to the "reversible addition-fragmentation chain transfer" technique.

The atom-transfer free-radical polymerization technique, also known by the abbreviation ATRP, consists in blocking the growing free-radical species in the form of a bond of C-halide type (in the presence of a metal/ligand complex). This type of polymerization is reflected by a control of the mass of the polymers formed and by a low polydispersity index.

In general, the atom-transfer free-radical polymerization is performed by polymerization of one or more free-radical-polymerizable monomers, in the presence of a primer having at least one transferable halogen atom,
of a compound comprising a transition metal capable of participating in a reduction step with the primer and a "dormant" polymer chain, and
of a ligand which may be chosen from compounds comprising a nitrogen (N), oxygen (O), phosphorus (P) or sulfur (S) atom, capable of coordinating via σ bonding to said compound comprising a transition metal, the formation of direct bonds between said compound comprising a transition metal and the polymer in formation being avoided.

The halogen atom is preferably a chlorine or bromine atom.

This process is described in particular in patent application WO 97/18247 and in the article by Matyjasezwski et al. published in *JACS*, 117, page 5614 (1995).

The technique of free-radical polymerization by reaction with a nitroxide consists in blocking the growing free-radical species in the form of a bond of C-ONR$_1$R$_2$ type, R$_1$ and R$_2$ possibly being independently of each other, an alkyl radical containing from 2 to 30 carbon atoms or together forming, with the nitrogen atom, a ring containing from 4 to 20 carbon atoms such as, for example, a 2,2,6,6-tetramethylpiperidyl ring. This polymerization technique is described especially in the articles "Synthesis of nitroxy-functionalized polybutadiene by anionic polymerization using a nitroxy-functionalized terminator", published in *Macromolecules* 1997, volume 30, pages 4238–4242, and "Macromolecular engineering via living free radical polymerizations" published in *Macromol. Chem. Phys.* 1998, vol. 199, pages 923–935, or in patent application WO-A-99/03894.

The RAFT (reversible addition-fragmentation chain transfer) polymerization technique consists in blocking the growing free-radical species in the form of a bond of C—S type. Dithio compounds such as thiobenzoates, dithiocarbamates or xanthan disulfides are used to do this. This technique is described in particular in patent application WO-A-98/58974 and in the article "A more versatile route to block copolymers and other polymers of complex architecture by living radical polymerization: the RAFT process", published in *Macromolecules*, 1999, volume 32, pages 2071–2074.

The nature and quality of the monomers, primers, compounds comprising the transition metal and the ligand(s) will be chosen by a person skilled in the art on the basis of his general knowledge according to the desired result.

The glass transition temperatures of the rigid and flexible blocks of the copolymers used in the present invention are measured by differential scanning calorimetry (DSC) according to ASTM standard D3418-97.

In order for the block copolymers defined above to have elastic properties that are advantageous for cosmetic use, the rigid blocks and the flexible blocks must be immiscible, that is to say mutually incompatible. This thermodynamic incompatibility is the absolutely essential condition for the formation of rigid block microdomaines acting as points for the physical crosslinking of the polymer network. These physical crosslinking points give the macromolecular system its elastic nature, that is to say its, at least partial, return to the initial state after stretching.

The physical parameter characterizing the elastic properties of the block copolymers above is their tensile recovery. This recovery is determined by a tensile creep test consisting in rapidly stretching a specimen to a predetermined degree of elongation, and then in releasing the stress and measuring the length of the specimen.

The creep test used to characterize the block copolymers of elastic nature of the present invention is performed in the following manner:

The specimen used is a film of the copolymer 500±50 μm thick, cut into 80 mm×15 mm strips. This copolymer film is obtained by drying, at a temperature of 22±2° C. and at a relative humidity of 50±5%, a 6% by weight solution or dispersion of said copolymer in water or ethanol.

Each strip is fixed between two jaws 50±1 mm apart, and is stretched at a speed of 20 mm/minute (under the temperature and relative humidity conditions above) up to an elongation of 50% ($\epsilon_{max}$), that is to say up to 1.5 times its initial length. The stress is then released by imposing a speed of return equal to the tensile speed, i.e. 20 mm/minute, and the elongation of the specimen (expressed as a percentage relative to the initial length) immediately after returning to zero loading ($\epsilon_i$) is measured.

The instantaneous recovery ($R_i$) is calculated with the aid of the following formula:

$$R_i(\%)=((\epsilon_{max}-\epsilon_i)/\epsilon_{max})\times 100$$

The value of the instantaneous recovery depends on many factors such as the nature, number, arrangement and relative proportion of the rigid and flexible blocks, or alternatively the molar mass of the polymer. The block copolymers of elastic nature of the present invention generally have an instantaneous recovery ($R_i$), measured under the conditions indicated above, of between 5% and 100%, preferably between 5% and 95%, more particularly between 10% and 90%, better still between 20% and 80% and ideally between 55% and 78%.

According to the present invention, each block may consist of one or more different types of monomer, that is to say that it may be a block of homopolymeric type or of random or alternating copolymer type. Each block, although possibly consisting of several different monomers, has only one glass transition temperature.

In the present invention, the difference between the glass transition temperatures of these two types of block, that is to say of the rigid blocks and the flexible blocks, is preferably at least equal to 20° C., especially between 20 and 160° C., in particular greater than or equal to 50° C., especially between 50° C. and 160° C. and ideally greater than or equal to 100° C., especially between 100 and 160° C.

The block ethylenic copolymers of elastic nature of the present invention may be chosen from diblock copolymers of formula AB, triblock copolymers of formula ABA or BAB, and polyblock copolymers of formula (AB)$_n$, B(AB)$_n$ or (AB)$_n$A, in which A represents a rigid block as defined above, B represents a flexible block as defined above and n is at least equal to two, preferably equal to 2 or 3, the blocks A of the same polymer possibly being identical or different and the blocks B of the same polymer possibly being identical or different.

In the present invention, it is most particularly preferred to use triblock copolymers of structure ABA, that is to say copolymers consisting of two identical or different rigid blocks (A), each having a glass transition temperature of greater than or equal to 20° C., surrounding a flexible central block (B) having a glass transition temperature of less than 20° C.

The blocks A (rigid) preferably represent from 10% to 60% by weight and in particular from 15% to 50% by weight of the final block copolymer and the blocks B (flexible) consequently preferably represent from 40% to 90% by weight and in particular from 50% to 85% by weight of the final block copolymer.

The block ethylenic copolymers of elastic nature used cosmetically in accordance with the present invention comprise at least one rigid block having a glass transition temperature ($T_g$) of greater than or equal to 20° C., and at least one flexible block having a glass transition temperature ($T_g$) of less than 20° C., consisting of units derived from one or more ethylenic monomers chosen from those of formula $$R^1R^2C=CR^3R^4 \qquad (I)$$

in which

R$^1$, R$^2$, R$^3$ and R$^4$ represent, independently of each other,
a hydrogen or halogen atom,
a $C_{1-20}$ alkyl group, which may be substituted with one or more halogen atoms or one or more OH groups,
a linear or branched α,β-unsaturated alkenyl or alkynyl group containing from 2 to 10 carbon atoms and possibly being substituted with one or more halogen atoms,
a $C_{3-8}$ cycloalkyl group which may be substituted with one or more halogen atoms,
a cyano group,
an aryl group,
a 4- to 12-membered heterocyclic group containing one or more N, O, S and P atoms,
a group —C(=Y)R$^5$, —CH$_2$C(=Y)R$^5$, —C(=Y)NR$^6$R$^7$, —YC(=Y)R$^5$, —NR$^6$C(=Y)R$^5$, —SOR$^5$, —SO$_2$R$^5$, —OSO$_2$R$^5$, —NR$^8$SO$_2$R$^5$, —PR$^5_2$, —P(=Y)R$^5_2$, —YPR$^5_2$, —YP(=Y)R$^5_2$ or —NR$^8_2$ optionally quaternized with an additional R$^8$, in which
Y represents a group NR$^8$, S or O,
R$^5$ represents an optionally hydroxylated $C_{1-20}$ alkyl, alkoxy or alkylthio, optionally etherified mono- or poly(alkyleneoxy), hydroxyl, —OM (with M=alkali metal), aryloxy or heterocyclyloxy group,
R$^6$ and R$^7$ represent, independently of each other, a hydrogen atom or a $C_{1-20}$ alkyl group or form, with the nitrogen atom to which they are attached, a 3- to 8-membered ring, and
R$^8$ represents a hydrogen atom or a $C_{1-20}$ alkyl or an aryl group,
a group —C(=O)—X—R$^9$—Z or —R$^9$—Z, in which
R$^9$ represents a saturated or unsaturated, linear, branched or cyclic, optionally halogenated $C_{1-20}$ hydrocarbon-based divalent radical possibly comprising one or more hetero atoms,
X represents a group NR$^{10}$ or an oxygen atom,
Z represents an —N(R$^{10}$)$_2$, —S—R$^{10}$ or P(R$^{10}$)$_2$ group in which each R$^{10}$ independently represents a saturated or unsaturated, linear, branched or cyclic, optionally halogenated $C_{1-20}$ hydrocarbon-based group possibly comprising one or more hetero atoms, the nitrogen atom of X and Z possibly being protonated or quaternized with $C_{1-20}$ alkyl radicals,
a group —R$^9$—NR$^{10}$-acid or —C(=O)—X—R$^9$—NR$^{10}$-acid in which acid represents a carboxylic, sulfonic or phosphonic acid function and R$^9$ and R$^{10}$ each have the meaning given above,
a radical comprising at least one silicon atom and especially —R-siloxane, —CONHR-siloxane, —COOR-siloxane or —OCO—R-siloxane radicals, in which R is a $C_{1-20}$ alkyl, alkylthio or alkoxy, aryloxy or heterocyclyloxy radical.

However, block copolymers with flexible blocks consisting exclusively of ethylene, propylene, butylene, butadiene and/or isoprene units are excluded from the present invention.

Preferably, the rigid block(s) of the block ethylenic copolymers of elastic nature of the present invention consist of units of one or more ethylenic monomers chosen from acrylic acid or methacrylic acid,
$C_{1-20}$ alkyl methacrylates containing a linear, branched, or cyclic chain, such as methyl methacrylate, ethyl methacrylate, propyl methacrylate, butyl methacrylate, isobutyl methacrylate, tert-butyl methacrylate and cyclohexyl methacrylate,
$C_{1-4}$ hydroxyalkyl methacrylates, such as 2-hydroxyethyl methacrylate and 2-hydroxylpropyl methacrylate,
certain vinyl esters such as vinyl acetate, vinyl propionate, vinyl benzoate and vinyl tert-butylbenzoate,
heterocyclic monomers, such as N-vinylpyrolidone, vinylcaprolactam, vinyl-N-($C_{1-6}$ alkyl)pyrroles, vinyloxazoles, vinylthiazoles, vinylpyrimidines and vinylimidazoles,
(meth)acrylamide,
certain aliphatic, cyclcaliphatic or aromatic methacrylamides, such as tert-butylacrylamide and di($C_{1-4}$ alkyl)methacrylamides,
styrene,
certain substituted styrenes,
(meth)acrylic or vinyl monomers containing a fluoro or perfluoro group, such as perfluorooctylethyl methacrylate, or (meth)acrylamides containing a fluoro or perfluoro group,
(meth)acrylic or vinyl silicone monomers, such as methacryloxypropyltris(trimethylsiloxy)silane, or silicone (meth)acrylamides,
acrylic or vinyl monomers comprising an optionally neutralized or quaternized amine function, such as dimethylaminoethyl (meth)acrylate, dimethylaminoethylmethacrylamide, vinylamine, vinylpyridine and diallyldimethylammonium chloride,
ethylenic carboxybetains or sulfobetaines obtained, for example, by quaternization of monomers containing ethylenic unsaturation comprising an amine function with sodium salts of a carboxylic acid containing a labile halogen (for example sodium chloroacetate) or with cyclic sulfones (for example propanesultone).

Examples of preferred rigid blocks which may be mentioned are poly(methyl methacrylate), polystyrene and poly (perfluorooctylethyl methacrylate) blocks.

Preferably, the flexible block(s) of the block ethylenic copolymers of elastic nature of the present invention consist of units derived from one or more ethylenic monomers chosen from $C_{1-20}$ alkyl acrylates containing a linear, branched or cyclic chain, such as methyl acrylate, ethyl acrylate, propyl acrylate, butyl acrylate, 2-ethylhexyl acrylate, isobutyl acrylate and tert-butyl acrylate,
$C_{6-20}$ aryl acrylates,
$C_{1-4}$ hydroxyalkyl acrylates, such as 2-hydroxyethyl acrylate and 2-hydroxypropyl acrylate,
mono-, di- or poly(ethylene glycol) (meth)acrylates containing an optionally etherified hydroxyl end, such as the (meth)acrylates of ethylene glycol, of diethylene glycol or of polyethylene glycol,
certain aliphatic, cycloaliphatic or aromatic (meth) acrylamides, such as undecylacrylamide or N-octylacrylamide, certain vinyl ethers such as vinyl isobutyl ether, certain substituted styrenes, acrylic or vinyl monomers containing a fluoro or perfluoro group, such as acrylic esters containing a perfluoroalkyl chain, for instance perfluorooctylethyl acrylate, acrylic or vinyl silicone monomers, such as acryloxypropylpolydimethylsiloxane.

Examples of preferred flexible blocks which may be mentioned are poly(butyl acrylate) and poly(2-ethylhexyl acrylate) blocks.

Polymers that are particularly advantageous for the cosmetic uses of the present invention are:

poly(methyl methacrylate-b-butyl acrylate-b-methyl methacrylate) triblock copolymers poly(methyl methacrylate-b-isobutyl acrylate-b-methyl methacrylate) triblock copolymers and poly(methyl methacrylate-b-butyl acrylate-b-styrene) triblock polymers.

A subject of the invention is also cosmetic compositions containing the block ethylenic copolymers of elastic nature described above.

These cosmetic compositions contain the elastic block ethylenic copolymers in dissolved or dispersed form in a suitable, physiologically acceptable solvent medium.

Examples of such solvents which may be mentioned include water, ketones such as methyl ethyl ketone, methyl isobutyl ketone, diisobutyl ketone, isophorone, cyclohexanone or acetone, lower alcohols such as ethanol, isopropanol, diacetone alcohol, 2-butoxyethanol or cyclohexanol, alkylene glycols such as ethylene glycol, propylene glycol or pentylene glycol, alkylene glycol ethers such as propylene glycol monomethyl ether, propylene glycol monomethyl ether acetate or dipropylene glycol monobutyl ether, $C_{2-7}$ alkyl acetates such as methyl acetate, ethyl acetate, propyl acetate, butyl acetate or isopentyl acetate, ethers such as dethyl ether, dimethyl ether or dichlorodiethyl ether, alkanes such as decane, heptane, dodecane or cyclohexane, aromatic hydrocarbons such as toluene and xylene, volatile oils such as cyclic or linear volatile silicone oils, hydrocarbon-based volatile oils such as isoparaffins, or fluoro oils.

The elastic block ethylenic copolymers are present in the cosmetic compositions in concentrations that depend on their chemical structure, but above all on the type of cosmetic composition. In general, this concentration of block copolymers of elastic nature is between 1% and 99% by weight, preferably between 5% and 50% by weight and better still between 7% and 40% by weight.

The cosmetic compositions of the present invention may also comprise a fatty phase composed of oils, gums and/or waxes.

The cosmetically acceptable oils, fatty substances that are liquid at room temperature (25° C.), may be hydrocarbon-based and/or silicone and/or fluoro oils. They may be of animal, plant, mineral or synthetic origin.

Mention may be made in particular, alone or as a mixture, of:

hydrocarbon-based oils of animal origin, such as perhydrosqualene, hydrocarbon-based plant oils, such as sunflower oil, corn oil, soybean oil, marrow oil, grape seed oil, ground nut oil, sweet almond oil, beauty-leaf oil, palm oil, sesame oil, hazelnut oil, apricot oil, macadamia oil, castor oil, avocado oil, jojoba oil and karite butter, liquid triglycerides of $C_{4-10}$ fatty acids, for instance heptanoic or octanoic acid triglycerides, caprylic/capric acid triglycerides, for instance those sold by the company Stearineries Dubois or those sold under the names Miglyol® 810, 812 and 818 by the company Dynamit Nobel, linear or branched hydrocarbons of mineral or synthetic origin, such as liquid paraffins and derivatives thereof, petroleum jelly, polydecenes, purcellin oil, or hydrogenated polyisobutene such as parleam, synthetic esters, in particular fatty acid esters, for instance the oils of formula $R^3COOR^4$ in which $R^3$ represents a higher fatty acid residue containing from 7 to 29 carbon atoms and $R^4$ represents a hydrocarbon-based chain containing from 3 to 30 carbon atoms, such as, for example, isopropyl myristate, 2-ethylhexyl palmitate, 2-octyldodecyl stearate, 2-octyldodecyl erucate and isostearyl isostearate, hydroxylated esters, such as isostearyl lactate, octyl hydroxystearate, octyl dodecyl hydroxystearate, diisostearyl malate and triisocetyl citrate, polyol esters, for instance propylene glycol dioctanoate, neopentyl glycol diheptanoate, diethylene glycol diisononanoate and pentaerythritol esters, fatty alcohols containing from 12 to 26 carbon atoms, for instance octyldodecanol, 2-butyloctanol, 2-hexyldecanol, 2-undecylpentadecanol and oleyl alcohol, partially fluorinated and/or siliconized hydrocarbon-based oils, silicone oils, such as volatile or nonvolatile, linear or cyclic polydimethylsiloxanes, alkyldimethicones, silicones modified with optionally fluorinated aliphatic and/or aromatic groups, or with functional groups such as hydroxyl, thiol and/or amine groups, and phenylsilicone oils such as polyphenylmethylsiloxanes or phenyltrimethicones.

The oils used may be volatile and/or nonvolatile. The term "volatile" means an oil capable of evaporating at room temperature from a support onto which it has been applied, in other words an oil having a measurable vapor pressure at 25° C. and at 1 atmosphere of greater than 0 Pa, in particular ranging from 0.13 to 40 000 Pa. Mention may be made especially of volatile silicone oils such as cyclic or linear volatile silicones, and cyclocopolymers. Mention may also be made of hydrocarbon-based volatile oils such as isoparaffins, and volatile fluoro oils.

Among the cosmetically acceptable gums and/or waxes which may be used, mention may be made of silicone gums, waxes of animal, plant, mineral or synthetic origin, such as microcrystalline waxes, paraffin, petrolatum, petroleum jelly, ozokerite, lignite wax, beeswax, lanolin and its derivatives, candelilla wax, ouricury wax, carnauba wax, Japan wax, cocoa butter, cork fiber wax, sugar cane wax, hydrogenated oils that are solid at 25° C., fatty esters and glycerides that are solid at room temperature, polyethylene waxes, waxes obtained by Fischer-Tropsch synthesis and lanolins, silicone waxes, and fluoro waxes.

The cosmetic compositions of the present invention may also contain one or more thickeners, one or more film-forming polymers and/or one or more plasticizers.

A particulate phase consisting of pigments and/or nacres and/or fillers may also be present in the cosmetic compositions of the present invention.

The term "pigments" should be understood as meaning white or colored, mineral or organic particles intended to color or opacify the composition. Mention may be made, for example, of titanium dioxide, zirconium dioxide or cerium dioxide, zinc oxide, iron oxide or chromium oxide, ferric blue, chromium hydrate, carbon black, ultramarines (aluminosilicate polysulfides), manganese pyrophosphate and certain metal powders such as silver or aluminum powders. Mention may also be made of certain lacquers such as calcium, barium, aluminum or zirconium salts. These pigments are generally present in a proportion of from 0% to 15% by weight and preferably in a proportion of from 8% to 10% of the final composition.

In the present invention, the term "fillers" means colorless or white, mineral or synthetic, lamellar or nonlamellar particles intended to give the composition body or rigidity and/or to give the make-up softness, a matt effect and uniformity. The fillers which may be used in the cosmetic compositions of the present invention are chosen, for example, from talc, mica, silica, kaolin, Nylon powder, polyethylene powder, Teflon®, starch, boron nitride, polymer microspheres such as Expancel® from the company Nobel industrie or Polytrap® from the company Dow Corning, silicone resin microbeads such as Tospearls® from the company Toshiba, precipitated calcium carbonate, magnesium carbonate, magnesium hydrocarbonate, and metal soaps derived from $C_{8-22}$ carboxylic acids.

The fillers are generally used in a proportion of from 0% to 80% by weight and preferably from 5% to 15% by weight relative to the final weight of the cosmetic composition.

The term "nacres" should be understood as meaning iridescent particles which reflect light. Mention may be made, for example, of natural mother-of-pearl, mica coated with titanium oxide, with iron oxide, with natural pigments or with bismuth oxychloride, and also colored titanium mica.

The nacres are generally present in a proportion of from 0% to 20% by weight and preferably in a proportion of from 8% to 15% by weight of the final cosmetic composition.

The composition may comprise a certain number of additives usually used in cosmetics, such as antioxidants, fragrances, essential oils, preserving agents, lipophilic or hydrophilic cosmetic active agents, moisturizers, vitamins, colorants, essential fatty acids, sphingolipids, self-tanning agents, sunscreens, antifoams, sequestering agents, antioxidants or free-radical scavengers.

Needless to say, a person skilled in the art will take care to select the optional additional compounds such that the advantageous properties of the composition according to the invention are not, or are virtually not, adversely affected by the envisaged addition.

The cosmetic compositions of the present invention containing the elastic block copolymers described above may be in any form usually encountered in cosmetics, that is to say in the form of a lotion, a suspension, a dispersion, an organic, aqueous or aqueous-alcoholic solution that is optionally thickened or gelled, a mousse, a spray, an oil-in-water, water-in-oil or multiple emulsion, a free, compact or cast powder, a solid or an anhydrous paste.

It may more particularly be a care, hygiene and/or make-up product. Preferred embodiments of the cosmetic compositions of the present invention are represented by hair compositions, especially styling compositions such as styling lacquers, gels or shampoos, nail varnishes and make-up compositions for the face, the body or integuments (nails, eyelashes, eyebrows or hair), such as an eyeshadow, a face powder, an eyeliner, a mascara, a free or compact powder, a foundation, a tinted cream, a lipstick, a concealer stick, etc.

The implementation examples which follow are given to illustrate the present invention, but have no limiting nature on the invention.

EXAMPLE 1

Preparation of a Difunctional Polymerization Primer

A difunctional primer is prepared according to the following reaction scheme:

HO—(CH$_2$)$_4$—OH +

2 C(CH$_3$)$_2$(Br)—C(=O)Br $\xrightarrow{\text{THF/triethylamine}}$ (CH$_3$)$_2$BrC—C(=O)—O—(CH$_2$)$_4$—O—C(=O)—C(CH$_3$)$_2$Br

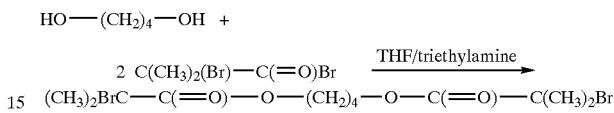

To do this, 18 g (0.2 mol) of 1,4-butanediol are mixed with 100 g of tetrahydrofuran and the mixture is left to equilibrate for 10 minutes at room temperature. 40.4 g (0.4 mol) of triethylamine are then added slowly, over a period of 30 minutes, such that the temperature of the solution does not increase suddenly. 92 g (0.4 mol) of 2-bromoisobutyryl bromide are then added very slowly, over a period of 3 hours and with cooling to 5° C. During this addition, a gradual yellowing of the reaction solution is observed.

The stirring is continued at 25° C. overnight and the temperature is then allowed to return gradually to room temperature.

The reaction solution is concentrated by evaporating off the THF, and the residue is precipitated from water. The aqueous phase is then extracted 3 times with ethyl ether, after which the ether phase is dried over magnesium sulfate.

After evaporating off the ether, 63 g of bis(n-butyl 1,4-bromoisobutyrate) are obtained, which corresponds to a yield of 80%.

EXAMPLE 2

Preparation of a poly(methyl methacrylate b-butyl acrylate-b-methyl methacrylate)triblock copolymer Step I: Polymerization of Butyl Acrylate 0.078 g (2×10$^{-4}$ mol) of difunctional primer prepared in Example 1, 2.9×10$^{-4}$ mol of CuBr, 5.7×10$^{-4}$ mol of 2,2'-bipyridine and 30 g of butyl acrylate are mixed together in a sealed reactor, in the absence of oxygen, and comprising a nitrogen inlet. The mixture is heated under a nitrogen atmosphere at a temperature of 120° C., the nitrogen inlet is closed and this temperature is maintained for 5 hours.

Step II: Polymerization of Methyl Methacrylate 12 g of methyl methacrylate are then added to the reaction mixture and the mixture is reacted for 3 hours at 120° C. and then allowed to cool to room temperature. 42 g of a viscous green solution are obtained, and are dissolved in about 100 ml of dichloromethane. This polymer solution is passed through a bed of neutral alumina and the clear solution is then precipitated from 5 volumes of a methanol/water mixture (80/20).

37 g of polymer are thus obtained in the form of a paste, which corresponds to a yield of 90% by weight.

The paste is washed with hot heptane to remove therefrom any residual monomers present.

The weight-average and number-average molar mass are determined by liquid chromatography by gel permeation (THF solvent, calibration curve established with linear polystyrene standards). The number-average molar mass ($M_n$) is equal to. 51 900 and the weight-average molar mass ($M_p$) is equal to 114 500.

The copolymer shows two glass transition temperatures $T_g$, the first at −47° C. attributable to the polybutyl acrylate block, and the second at 70° C. attributable to the poly (methyl methacrylate) blocks.

The instantaneous recovery of the copolymer is 75%.

EXAMPLE 3

Preparation of a Lacquer

An aerosol is prepared with 100 g of a solution containing 9% by weight of the polymer prepared in Example 2 in ethanol and 75 g of dimethyl ether as propellant gas.

The composition is sprayed onto locks of chestnut-brown hair 18 cm long, and the hold of the hair style and the suppleness of the locks are evaluated by a panel of 5 individuals, using a grading scale ranging from 0 (poor) to 5 (excellent). The grades obtained are 4 for the hold of the hair style and 4 for the suppleness of the locks.

EXAMPLE 4

Preparation of a Nail Varnish

The polymer obtained in Example 2 is dissolved, at a rate of 25% by weight, in ethyl acetate.

The solution is applied in the usual manner to the nails. The dried varnish shows good resistance to ageing. It does not become worn and remains glossy. It is readily removed with standard acetone-based solvents.

What is claimed is:

1. A method of making a cosmetic composition comprising incorporating block ethylenic copolymers of elastic nature into said composition, said block ethylenic copolymers of elastic nature comprising
   (a) at least one rigid block (A) having a glass transition temperature ($T_g$) of greater than or equal to 20° C., consisting of units derived from one or more ethylenic monomers, and
   (b) at least one flexible block (B) having a glass transition temperature ($T_g$) of less than 20° C., consisting of units derived from one or more ethylenic monomers,
   said copolymers allowing the production of a film having an instantaneous recovery of between 5% and 100% with the exclusion of block copolymers having flexible blocks consisting exclusively of ethylene, propylene, butylene, butadiene and/or isoprene units.

2. The method of claim 1, characterized in that the block ethylenic copolymers of elastic nature are polymers obtained by controlled free-radical polymerization.

3. The method of claim 1, characterized in that said rigid block having a glass transition temperature ($T_g$) of greater than or equal to 20° C. consists of units derived from one or more ethylenic monomers chosen from acrylic acid or methacrylic acid, $C_{1-20}$ alkyl methacrylates containing a linear, branched or cyclic chain, $C_{1-4}$ hydroxyalkyl methacrylates, vinyl esters, heterocyclic monomers, (meth) acrylamide, aliphatic, cycloaliphatic or aromatic methacrylamides, styrene, substituted styrenes, (meth) acrylic or vinyl monomers containing a fluoro or perfluoro group or (meth)acrylamides containing a fluoro or perfluoro group, (meth)acrylic or vinyl silicone monomers or silicone (meth)acrylamides, acrylic or vinyl monomers comprising an amine that is optionally neutralized or quaternized, and ethylenic carboxybetaines or sulfobetaines.

4. The method of claim 1, characterized in that said flexible block having a glass transition temperature ($T_g$) of less than 20° C. consists of units derived from one or more ethylenic monomers chosen from $C_{1-20}$ alkyl acrylates containing a linear, branched or cyclic chain, $C_{6-20}$ aryl acrylates, $C_{1-4}$ hydroxyalkyl acrylates, mono-, di- or poly (ethylene glycol) (meth)acrylates containing an optionally etherified hydroxyl end, aliphatic, cycloaliphatic or aromatic (meth)acrylamides, certain vinyl ethers, substituted styrenes, acrylic or vinyl monomers containing a fluoro or perfluoro group, and acrylic or vinyl silicone monomers.

5. The method of claim 1, characterized in that the block ethylenic copolymers are chosen from diblock copolymers of formula AB, triblock copolymers of formula ABA or BAB and polyblock copolymers of formula $(AB)_n$, $B(AB)_n$ or $(AB)_nA$, in which each A represents a rigid block having a glass transition temperature of greater than or equal to room temperature (20° C.), each B represents a flexible block having a glass transition temperature of less than room temperature (20° C.) and n is at least equal to two, the blocks A of the same polymer possibly being identical or different, and the blocks B of the same polymer possibly being identical or different.

6. The method of claim 5, characterized in that said ethylenic copolymers are triblock copolymers of formula ABA in which each A independently represents a rigid block having a glass transition temperature of greater than or equal to room temperature (20° C.) and B represents a flexible block having a glass transition temperature which is less than room temperature (20° C.).

7. The method of claim 1, characterized in that the block ethylenic copolymers are chosen from
   poly(methyl methacrylate-b-butyl acrylate-b-methyl methacrylate) triblock copolymers
   poly(methyl methacrylate-b-isobutyl acrylate-b-methyl methacrylate) triblock copolymers and
   poly(methyl methacrylate-b-butyl acrylate-b-styrene) triblock polymers.

8. The method of claim 1, characterized in that the rigid blocks A are immiscible, with the flexible blocks B.

9. The method of claim 1, characterized in that the difference between the glass transition temperatures of the rigid blocks and the flexible blocks is at least equal to 20° C.

10. The method of claim 1, characterized in that said block polymers have an instantaneous recovery of between 5% and 95%.

11. The method of claim 1, characterized in that the blocks A represent from 10% to 60% by weight of the final block copolymer and the blocks B represent from 40% to 90% by weight of the final block copolymer.

12. A cosmetic composition comprising, in a physiologically acceptable medium, at least one block ethylenic copolymer of elastic nature comprising
   (a) at least one rigid block (A) shaving a glass transition temperature ($T_g$) of greater than or equal to 20° C., consisting of units derived from one or more ethylenic monomers, and
   (b) at least one flexible block (B) having a glass transition temperature ($T_g$) of less than 20° C., consisting of units derived from one or more ethylenic monomers,
   said copolymers allowing the production of a film having an instantaneous recovery of between 5% and 100% with the exclusion of block copolymers having flexible blocks consisting exclusively of ethylene, propylene, butylene, butadiene and/or isoprene units.

13. The cosmetic composition as claimed in claim 12, characterized in that the block ethylenic copolymers of elastic nature are polymers obtained by controlled free-radical polymerization.

14. The composition as claimed in claim 12, characterized in that said rigid block having a glass transition temperature ($T_g$) of greater than or equal to 20° C. consists of units derived from one or more ethylenic monomers chosen from acrylic acid or methacrylic acid, $C_{1-20}$ alkyl methacrylates containing a linear, branched or cyclic chain, $C_{1-4}$ hydroxyalkyl methacrylates, certain vinyl esters, heterocyclic monomers, (meth)acrylamide, aliphatic, cycloaliphatic or aromatic methacrylamides, styrene, substituted styrenes, (meth)acrylic or vinyl monomers containing a fluoro or perfluoro group or (meth)acrylamides containing a fluoro or perfluoro group, (meth)acrylic or vinyl silicone monomers or silicone (meth)acrylamides, acrylic or vinyl monomers comprising an amine that is optionally neutralized or quaternized, and ethylenic carboxybetaines or sulfobetaines.

15. The cosmetic composition as claimed in claim 12, characterized in that said flexible block having a glass transition temperature ($T_g$) of less than 20° C. consists of units derived from one or more ethylenic monomers chosen from $C_{1-20}$ alkyl acrylates containing a linear, branched or cyclic chain, $C_{6-20}$ aryl acrylates, $C_{1-4}$ hydroxyalkyl acrylates, mono-, di- or poly(ethylene glycol) (meth)acrylates containing an optionally etherified hydroxyl end, aliphatic, cycloaliphatic or aromatic (meth)acrylamides, vinyl ethers, substituted styrenes, acrylic or vinyl monomers containing a fluoro or perfluoro group, and acrylic or vinyl silicone monomers.

16. The cosmetic composition as claimed in claim 12, characterized in that the block ethylenic copolymers are chosen from diblock copolymers of formula AB, triblock copolymers of formula ABA or BAB and polyblock copolymers of formula $(AB)_n$, in which each A represents a rigid block having a glass transition temperature of greater than or equal to room temperature (20° C.), each B represents a flexible block having a glass transition temperature of less than room temperature (20° C.) and n is at least equal to two, the blocks A of the same polymer possibly being identical or different, and the blocks B of the same polymer possibly being identical or different.

17. The compositions as claimed in claim 12, characterized in that the ethylenic copolymers are triblock copolymers of formula ABA in which each A independently represents a rigid block having a glass transition temperature of greater than or equal to room temperature (20° C.) and B represents a flexible block having a glass transition temperature which is less than room temperature (20° C.).

18. The composition as claimed in claim 12, characterized in that the rigid blocks A are immiscible, with the flexible blocks B.

19. The cosmetic composition as claimed in claim 12, characterized in that the ethylenic copolymers are chosen from
poly(methyl methacrylate-b-butyl acrylate-b-methyl methacrylate) triblock copolymers
poly(methyl methacrylate-b-isobutyl acrylate-b-methyl methacrylate) triblock copolymers and
poly(methyl methacrylate-b-butyl acrylate-b-styrene) triblock polymers.

20. The composition as claimed in claim 12, characterized in that the difference between the glass transition temperatures of the rigid blocks and the flexible blocks is at least equal to 20° C.

21. The composition as claimed in claim 12, characterized in that said block polymers of elastic nature have an instantaneous recovery of between 5% and 95%.

22. The composition as claimed in claim 12, characterized in that the blocks A represent from 10% to 60% by weight of the final block copolymer and the blocks B represent from 40% to 90% by weight the final block copolymer.

23. The cosmetic composition as claimed in claim 12, characterized in that it contains from 1% to 99% by weight, of said block copolymers of elastic nature.

24. The composition as claimed in claim 12, characterized in that said physiologically acceptable medium comprises one or more suitable solvents chosen from water, ketones, alcohols, alkylene glycols, alkylene glycol ethers, $C_{2-7}$ alkyl acetates, ethers, alkanes, aromatic hydrocarbons, aldehydes and volatile oils.

25. The cosmetic composition as claimed claim 12, characterized in that said physiologically acceptable medium also comprises a fatty phase composed of fatty substances that are liquid or solid at room temperature, of animal, plant, mineral or synthetic origin.

26. The cosmetic composition as claimed in claim 12, characterized in that said physiologically acceptable medium also comprises one or more thickeners, one or more film-forming polymers and/or one or more plasticizers.

27. The cosmetic composition as claimed in claim 12, characterized in that said physiologically acceptable medium also comprises a particulate phase consisting of pigments and/or nacres and/or fillers.

28. The cosmetic composition as claimed in claim 12, characterized in that said physiologically acceptable medium also comprises one or more additives such as fragrances, essential oils, preserving agents, lipophilic or hydrophilic cosmetic active agents, moisturizers, vitamins, colorants, essential fatty acids, sphingolipids, self-tanning agents, sunscreens, antifoams, sequestering agents, or free-radical scavengers.

29. The cosmetic composition as claimed in claim 12, characterized in that it is in the form of a lotion, a suspension, a dispersion, an organic, aqueous or aqueous-alcoholic solution that is optionally thickened or gelled, a mousse, a spray, an oil-in-water, water-in-oil or multiple emulsion, a free, compact or cast powder, a solid or an anhydrous paste.

30. The cosmetic composition as claimed in claim 12, characterized in that it is a hair lacquer.

31. The cosmetic composition as claimed in claim 12, characterized in that it is a nail varnish.

32. The cosmetic composition as claimed in claim 12, characterized in that it is a make-up composition.

33. The method of claim 1, to improve the styling power and suppleness of a hair lacquer.

34. The method of claim 1, to increase the impact strength of a nail varnish.

35. The method of claim 1, to improve the hold of a make-up composition.

36. The method of claim 5 characterized in that n is equal to 2 or 3.

37. The method of claim 9 characterized in that said difference is greater than 50° C.

38. The method of claim 9 characterized in that said difference is greater than 100° C.

39. The method of claim 10 characterized in that said recovery is between 10% and 90%.

40. The method of claim 10 characterized in that said recovery is between 20% and 80%.

41. The method of claim 10 characterized in that said recovery is between 55% and 78%.

42. The method of claim 11 characterized in that the blocks A represent from 15% to 50% by weight of the final block copolymer and the blocks B represent from 50% to 85% by weight of the final block copolymer.

43. The composition of claim 16 characterized in that n is equal to 2 or 3.

44. The composition of claim 20 characterized in that said difference is greater than 50° C.

45. The composition of claim 20 characterized in that said difference is greater than 100° C.

46. The composition of claim 21 characterized in that said recovery is between 10% and 90%.

47. The composition of claim 21 characterized in that said recovery is between 20% and 80%.

48. The composition of claim 21 characterized in that said recovery is between 55% and 78%.

49. The composition of claim 22 characterized in that the blocks A represent from 15% to 50% by weight of the final block copolymer and the blocks B represent from 50% to 85% by weight of the final block copolymer.

50. The composition of claim 23 characterized in that it contains from 5% to 50% by weight of said block copolymers of elastic nature.

51. The composition of claim 23 characterized in that it contains from 7% to 40% by weight of said block copolymers of elastic nature.

* * * * *